United States Patent [19]
Richards

[11] Patent Number: 5,614,501
[45] Date of Patent: Mar. 25, 1997

[54] COMPOSITIONS AND METHODS FOR ANIMAL HUSBANDRY AND FOR TREATING GASTROINTESTINAL DISORDERS

[75] Inventor: Geoffrey N. Richards, Missoula, Mont.

[73] Assignee: The University of Montana, Missoula, Mont.

[21] Appl. No.: 434,492

[22] Filed: May 4, 1995

Related U.S. Application Data

[62] Division of Ser. No. 278,414, Jul. 21, 1994.
[51] Int. Cl.$^6$ .......................... A61K 31/70; A61K 31/715
[52] U.S. Cl. ........................ 514/22; 514/23; 514/53; 514/57; 514/458; 514/867
[58] Field of Search ........................ 514/22, 23, 53, 514/57, 458, 867

[56] References Cited

U.S. PATENT DOCUMENTS

| | | | |
|---|---|---|---|
| 4,857,327 | 8/1989 | Virdalm | 424/195.1 |
| 4,927,811 | 2/1990 | Quarles | 514/23 |
| 5,043,160 | 8/1991 | Würsch | 424/195.1 |

FOREIGN PATENT DOCUMENTS

| | | | |
|---|---|---|---|
| 0138784 | 4/1985 | European Pat. Off. . | |
| 0138784A2 | 4/1985 | European Pat. Off. | A61K 31/715 |
| 214317 | 3/1987 | European Pat. Off. . | |
| 0214317A1 | 3/1987 | European Pat. Off. | A23L 1/308 |
| 0425272 | 5/1991 | European Pat. Off. . | |
| 0425272A1 | 5/1991 | European Pat. Off. | A23L 1/308 |
| 3622896 | 1/1988 | Germany . | |
| 3622896A1 | 1/1988 | Germany | A61K 31/79 |
| 6-219953 | 8/1994 | Japan | A23K 1/12 |
| WO85/01441 | 4/1985 | WIPO | A61K 35/78 |
| WO94/27618 | 12/1994 | WIPO . | |

OTHER PUBLICATIONS

Yamada et al., "Advances in Cereal Chemistry and Technology in Japan", Cereal Foods, Jul. 1993, pp. 490–492.

Journal of Ethnopharmacology, vol. 36, Heinrich et al., "Indigenous Phytotherapy of Gastrointestinal Disorders . . . Ethnopharmacologic Evaluation", 1992, pp. 63–80.

Journal of Pharmacy and Pharmacology, vol. 45, No. 2, Galvez et al., "Anitdiarrhoeic Activity of Quercitrin in Mice and Rats", Feb. 1992, pp. 157–159.

Cereal Foods, Yamada et al., "Advances in Cereal Chemistry and Technology in Japan", Jul. 1993, pp. 490–492.

Galves, J., et al. "*Antidiarrhoeic activity of quercitrin in mice and rats*", J. Pharm Pharmacol, Feb. 1993, 45:157–159.

Heinrich, M., et al., "*Indigenous phytotherapy of gastrointestinal disorders in a lowland Mixe community (Oaxaca, Mexicol; Ethnopharmacologic evaluation*", Journal of Ethnopharmacology, 36 (1992) 63–80.

Hara Hiroyoshi et al., "Effect of Tea Polyphenols on Fecal Flora and Fecal Metabolic Products of Pigs," *J. Vet. Med. Sci.* 57:45–49 (1995).

von Haastrecht, Jos., "Promising Performers," *Food R&D* 38–39 (1995).

*Primary Examiner*—Gary Geist
*Assistant Examiner*—Rosalynd A. Williams
*Attorney, Agent, or Firm*—Arnall Golden & Gregory

[57] ABSTRACT

Compositions containing hemicelluloses in combination with polyphenols, methods of preparing the compositions, and methods of treating humans or animals with the composition are provided. Also provided is a method for increasing growth rate, improving feed efficiency and decreasing scour after weaning in an animal by administering an effective amount of the composition to the animal. The hemicelluloses preferably are not consumed by human alimentary enzymes or harmful bacteria, such as putrefactive or pathogenic bacteria, in the gastrointestinal tract, and are consumed by beneficial bacteria, such as bifidobacteria, in the gastrointestinal tract. The polyphenols preferably decrease the amount of harmful bacteria in the gastrointestinal tract. The compositions can optionally contain a carrier or be used as a feed addition and are administered to humans or other animals in an amount sufficient to treat the gastrointestinal disorder.

15 Claims, No Drawings

COMPOSITIONS AND METHODS FOR ANIMAL HUSBANDRY AND FOR TREATING GASTROINTESTINAL DISORDERS

This is a divisional of U.S. Ser. No. 08/278,414 filed on July 21, 1994, by Geoffrey N. Richards entitled Compositions and Methods for Animal Husbandry and for Treating Gastrointestinal Disorders.

This invention is in the area of animal feed additives.

BACKGROUND OF THE INVENTION

Several gastrointestinal disorders, including diarrhea, can be caused by an imbalance in the normal gut flora, usually an increase in harmful bacteria, including pathogenic and putrefactive bacteria such as Clostridium and Bacteroideceae, and/or a decrease in beneficial, acid-forming bacteria such as bifidobacteria.

Antibiotics have been used to treat diarrhea. A major drawback of using antibiotics is that they can be non-selective, killing both the harmful bacteria and the beneficial bacteria.

Diarrhea is also treated with drugs such as Loperamide HCl, commonly sold under the name Immodium™, and codeins that act on the smooth muscle in the walls of the gastrointestinal tract to inhibit peristalsis, the rhythmic waves of muscular contraction that move the contents of the GI tubes. These drugs are effective to treat the symptoms of diarrhea, which typically include increased force and rate of peristalsis. A major limitation, however, is that the cause of the diarrhea is not treated.

Another approach to treating gastrointestinal disorders involves coating the gastrointestinal tract with a composition containing bismuth salicylate, for example, Pepto-Bismol™. The limitation with this method of treatment is that bismuth salicylate is not always very effective at treating the symptoms of diarrhea, and does not treat the cause of diarrhea.

Gastrointestinal disorders have also been treated with dietary fiber. Dietary fiber is a general term covering a number of substances, including cellulose, hemicellulose, oligosaccharides, pectins, gums, waxes, and lignin. A more general definition is "endogenous components of plant materials in the diet that are resistant to digestion by human (intestinal) enzymes, i.e., mainly non-starch polysaccharides and lignin." Grant-Thompson., W., "The Fibre Story," in *Gut Reactions, Understanding Symptoms in the Digestive Tract,* Plenum Press, N.Y., pp. 59 (1989). Dietary fiber can be either soluble or insoluble.

Dietary fiber resists hydrolysis by human alimentary enzymes, but can be fermented by colonic microflora. In general, soluble fiber is more readily fermented than insoluble fiber. The main physiological effects of these substances are on gastric emptying and colonic transit time, and can result in improved glucose tolerance and decreased starch digestion. The fermentation of dietary fiber results in increased bacterial biomass, increased fecal mass, lowering of intracolonic pH due to production of short chain fatty acids, and production of various gases as metabolic end products. One limitation of using dietary fiber is that it can decrease the absorption of vitamins in certain individuals.

Another limitation to using dietary fiber, generally, is that certain dietary fibers are fermented by both harmful and beneficial bacteria. For example, lactulose is used clinically to enrich intestinal sugar sources, since lactulose is not digested or absorbed in human intestines, and reaches the ileum intact. While lactulose is digested by bifidobacteria, it is also digested by other intestinal bacteria, such as *Escherichia Coli,* and sometimes causes diarrhea. Yawaza, K., and Tamura, Z., *Bifidobacteria Microflora,* 1(1):39–44 (1982). Other examples of dietary fiber that is digested by both beneficial and harmful bacteria are described in Yamada, H., et al., *Cereal Foods World,* 38(7):490–492, 491 (1993).

Some dietary fibers are selectively fermented by bifidobacteria, a beneficial bacteria that produces acetic and lactic acid from sugar. An example of this type of dietary fiber is wheat bran hemicellulose, which is composed mainly of arabinoxylans. Yamada, H., et al., *Cereal Foods World,* 38(7):490–492 (1993). Wheat bran hemicellulose apparently also suppresses the proliferation of harmful bacteria, such as *Escherichia Coli.* The acid produced by the bifidobacteria suppresses the adsorption of ammonia and amines produced by putrefactive bacteria such as Clostridium.

Inulin and fructose oligosaccharides have been shown to have bifidogenic factors, but it is unclear why these oligosaccharides are primarily fermented by bifidobacteria. Roberfroid, M., *Critical Reviews in Food Science and Nutrition,* 33(2);103–148 (1993). Transglycosylated disaccharides have also been shown to increase the amount of fecal bifidobacteria and lactobacilli, and decrease the amount of Bacteroidacea and Candida spp. in the feces. Ito, M., et al., *J. Nutr. Sci. Vitaminol.,* 39:279–288 (1993).

Certain compounds can be useful to treat gastrointestinal disorders because they selectively eliminate harmful bacteria. Some polyphenols have been reported to be useful for this purpose. Certain plants containing polyphenols have been used to treat gastrointestinal disorders. Baldi, A., et al., *Planta Medica,* 58, Supplemental Issue 1, pp. A691 (1992).

Polyphenols (especially flavonoids, for example, compounds with a phenyl-$C_3$-phenyl structure, wherein the phenyl rings are functionalized with one or more hydroxy groups) derived from green tea have been reported to significantly decrease the amount of *Clostridium perfrigens* and other Clostridium spp. (putrefactive bacteria), and significantly increase the amount of Bifidobacterium spp. (acid forming bacteria) in human feces. Okubo, T., et al., *Biosci. Biotech. Biochem.,* 56(4):588–591 (1992).

It is therefore an object of the present invention to provide compositions and methods for treating gastrointestinal disorders in humans and animals.

It is a further object of the present invention to provide an inexpensive feed additive that aids digestion and/or prevents gastrointestinal disorders.

It is yet a further object of the present invention to provide a method for preparing a feed additive composition containing arabinogalactan and polyphenols.

SUMMARY OF THE INVENTION

Compositions and methods for treating gastrointestinal disorders, including diarrhea, in animals and humans are described. The compositions include a dietary fiber in coordination with polyphenol(s). It is believed that the composition acts by increasing the amount of beneficial bacteria, such as bifidobacteria, and reducing the amount of putrefactive and pathogenic bacteria, such as Clostridium.

Preferably, the dietary fiber is one or more of cellulose, hemicellulose, oligosaccharides, galactomannan, pectins, gums, waxes, or lignin. Soluble fibers are preferred over insoluble fibers. Hemicellulose is a preferred dietary fiber. Arabinogalactan, especially arabinogalactan derived from trees of the genus Larix, is a preferred hemicellulose. The preferred molecular weight average of the hemicellulose is between 3,000 and 2,500,000, more preferably between 3,000 and 100,000.

The polyphenols have a preferred molecular weight between 280 and 6,000. The ratio by weight of dietary fiber/polyphenols is preferably between 20 and 3.

Preferred animals to be treated include, but are not limited to humans, pigs, poultry, calves, horses and domestic pets. The composition preferably is administered to animals as a food additive, at a dosage level of between 0.1 to 5% by weight of feed, preferably between 0.1 and 2% by weight of feed. Preferably, the composition is administered to humans as a powder added to foodstuff formulations or to drinks.

DETAILED DESCRIPTION OF THE INVENTION

A composition and method is provided for treating human gastrointestinal disorders or other disorders in which beneficial moderation of the intestinal microflora or an increase in large intestine pH is sought. The composition can also be used to increase the growth rate and to improve feed conversion in animals and to ameliorate or cure scours or diarrhea, and also to improve and maintain general health.

The composition contains a dietary fiber in combination with polyphenol(s). The composition is administered orally to a human or animal in need of treatment of a gastrointestinal disorder, such as diarrhea. The composition is believed to lower the concentration of harmful bacteria, for example, putrefactive and pathogenic bacteria, and increase the concentration of beneficial bacteria, such as bifidobacteria.

As used herein, harmful bacteria are defined as those bacteria which cause gastrointestinal disorders, and include but are not limited to putrefactive and pathogenic bacteria. Putrefactive and pathogenic bacteria are defined as those bacteria that raise colonic pH by producing amines and/or ammonia, p-cresol, and indole. Types of these bacteria include but are not limited to Clostridium spp., Bacteroidaceae, and Candida spp.

As used herein, beneficial bacteria are defined as those which increase the amount of small chain fatty acids, such as lactic acid, propionic acid, acetic acid. A non-limiting example of a beneficial bacteria is bifidobacteria.

A. Dietary Fiber

As used herein, dietary fiber is defined as endogenous components of plant materials in the diet that are resistant to digestion by human or other animal (intestinal) enzymes. Dietary fibers include but are not limited to cellulose, hemicellulose, oligosaccharides, pectins, gums, waxes, and lignin. The dietary fiber can be soluble or insoluble, but soluble fibers are preferred. Soluble fiber is defined as fiber that is soluble in water, and insoluble fiber is defined as a fiber that is insoluble in water. It is also preferable that the dietary fiber is highly branched, for example, more than one branch per 100 in-chain units.

Hemicellulose is a preferred dietary fiber. As used herein, hemicellulose is defined as a polysaccharide found in plant cell walls in association with cellulose and lignin, that is soluble in and extractable by dilute alkaline solutions. Preferred average molecular weight ranges for hemicelluloses are between 3,000 and 2,500,000, more preferably, between 3,000 and 100,000. Most preferably, the hemicellulose is not digested by human alimentary enzymes, reaches the ileum and large intestine largely intact, is not digested by bacteria other than bifidobacteria, and is an efficient sugar source for bifidobacteria. The hemicellulose is preferably soluble in aqueous solutions at a pH less than or equal to 8.

Arabinogalactan is a preferred hemicellulose. As used herein, an arabinogalactan is defined as an oligosaccharide containing a β-(1,3)-linked galactan backbone with side chains containing arabinose and galactose. Preferably, the average molecular weight is between 3,000 and 2,500,000, and more preferably, between 3,000 and 100,000. Preferred arabinogalactans are those derived from Larix trees. Preferably, the ratio of arabino groups to galactose groups is between 0.1:1 and 1:1.

Several dietary fibers are known to have bifidogenic factors. These fibers include but are not limited to arabinoxylan, galactomannan, inulin, fructose oligosaccharide, transglycosylated oligosaccharides, and wheat bran hemicellulose. Compositions containing one or more of these fibers in combination with polyphenols are also preferred embodiments.

B. Polyphenols

As used herein, polyphenols are defined as molecules with two or more phenol moieties. Useful polyphenols include flavonoids, such as tannins, aromadendrines, anthocyanins, catecholins, catechins and taxifolins. Taxifolin is a preferred polyphenol since it is found in the Larix tree, which also contains arabinogalactan, a preferred dietary fiber.

Preferably, the polyphenol lowers the amount of harmful bacteria, such as Clostridium, without lowering the amount of beneficial bacteria, such as bifidobacteria. Preferred polyphenols have a molecular weight range of between 280 and 6,000.

C. Preparation of Arabinogalactan Containing Polyphenols

In a typical process for preparing arabinogalactan, wood from a tree of the genus Larix, for example, *Larix occidentalix* Nuttall (Western Latch), is chipped or pulverized. The arabinogalactan is then extracted with warm water. Polyphenols, including taxifolins, are also extracted by this process. To prepare purified arabinogalactan, the polyphenols are removed, for example, by reacting the crude extract with MgO. However, retention of the polyphenols is desired, since both the dietary fiber and the polyphenols are useful for treating gastrointestinal disorders. The process can be optimized for maximum extraction of polyphenols by increasing the water temperature and/or by raising the pH to between 7 and 12 by adding a base such as ammonia, or sodium, calcium or pottasium hydroxide.

D. Dietary Fiber-Polyphenol composition

Dietary fiber and polyphenols are preferably combined by mixing. The ratio of fiber/polyphenol by weight in the composition is preferably between 20 and 3. This composition can optionally be combined with a carrier that is pharmaceutically acceptable for oral administration. When combined with a carrier, the weight percent of the composition/carrier is preferably between 1 and 10. Typical carriers are food and water. If soluble fiber is used, the combination of an aqueous carrier and the fiber will be a solution. If insoluble fiber is used, the combination of an aqueous carrier and the fiber will be a suspension.

The compositions can include an inert diluent or an edible carrier. They may be enclosed in gelatin capsules or compressed into tablets. For the purpose of oral therapeutic administration, the composition can be incorporated with excipients and used in the form of tablets, troches, suppositories or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The composition can be administered as a component of an elixir, suspension, syrup, wafer, chewing gum or the like. A syrup may contain, in addition to the active compounds, sucrose as a sweetening agent and certain preservatives, dyes and colorings and flavors.

E. Treatment of Gastrointestinal Disorders

The composition is useful to treat gastrointestinal disorders, such as diarrhea. The composition is administered to a human or animal in need of treatment thereof. Gastrointestinal disorders are well known to those in the art. Examples of gastrointestinal disorders include but are not limited to diarrhea, distension of the abdomen, diverticulitis, constipation, and irritable bowel syndrome. Several gastrointestinal disorders are known to be caused by an increase in harmful bacteria, or a decrease in beneficial bacteria in the gastrointestinal tract.

The composition is also useful to treat hepatic encephalotomy associated with cirrhosis of the liver.

Typical systemic dosages for treatment of gastrointestinal disorders are those ranging from 10 mg/kg to 300 mg/kg per day as a single daily dose or divided daily doses.

The composition is administered for a sufficient time period to alleviate the undesired symptoms and the clinical signs associated with the gastrointestinal disorder being treated.

The concentration of the components in the composition will depend on absorption, inactivation, and excretion rates of the components as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the dosage ranges set forth herein are exemplary only and are not intended to limit the scope or practice of the claimed composition.

The composition can also be mixed with other active materials which do not impair the desired action, or with materials that supplement the desired action, such as compounds that treat the symptoms of peristalsis.

Because intake of dietary fiber may adversely affect the absorption of vitamins and minerals in certain individuals, it can be desirable to combine the composition with a vitamin and/or mineral supplement.

Incorporation into Animal Feed

The dietary fiber-polyphenol composition can be added to animal feed. Animal feeds include but are not limited to poultry feed, swine feed, horse feed, feed for early-weaned calves, and dog and cat food.

Typical dosage ranges are between 0.1 to 5% by weight of the animal feed, preferably between 0.1 and 2% by weight of the animal feed. By increasing the amount of beneficial bacteria, and lowering the amount of harmful bacteria, the health, feed conversion efficiency and growth rate of the animal are expected to increase. Diarrhea, especially during and after weaning, will decrease.

This invention has been described with reference to its preferred embodiments. Variations and modifications of the invention will be obvious to those skilled in the art from the foregoing detailed description of the invention. It is intended that all of these variations and modifications be included within the scope of the appended claims.

We claim:

1. A method for increasing growth rate, improving feed efficiency and decreasing scour after weaning in an animal, the method comprising administering to the animal an effective amount of a composition comprising an extract of wood of a tree of the genus Larix comprising arabinogalactan and a polyphenol, wherein thee arabinogalactan is water soluble, resists digestion by animal alimentary enzymes, and is selectively digested by Bifidobacteria.

2. The method of claim 1 wherein the polyphenol contains at least three phenol moieties and has a molecular weight of between 280 and 6,000.

3. The method of claim 2 wherein the tree is a Western Larch tree.

4. The method of claim 1 wherein the polyphenol is a flavonoid.

5. The method of claim 4 wherein the flavonoid is selected from the group consisting of tannins, taxifolins, catecholines, anthocyanins and catechins.

6. The method of claim 1 wherein the composition is administered in a dosage of between 10 and 300 mg/kg body weight.

7. The method of claim 1 further comprising adding a carrier to the composition.

8. The method of claim 7 wherein the carrier is food.

9. The method of claim 8 wherein the composition is added to food in a concentration effective to increase the relative ratio of Bifidobacteria to Clostridia.

10. The method of claim 8 wherein the composition is added to food in a concentration of between 0.1 and 5% by weight of the food.

11. The method of claim 8 wherein the composition is added to food in a concentration of between 0.1 and 2% by weight of the food.

12. The method of claim 1 wherein the animal is selected from the group consisting of poultry, swine, horses, calves, dogs and cats.

13. The method of claim 5 wherein the polyphenol is taxifolin.

14. The method of claim 13 wherein the plant extract containing arabinogalactan and a polyphenol is isolated from a tree of the genus Larix by extraction of chipped or pulverized wood of the tree with water.

15. The method of claim 14 wherein the water has a pH between about 7 and 12.

* * * * *